United States Patent [19]

Wallace

[11] Patent Number: 4,863,423

[45] Date of Patent: Sep. 5, 1989

[54] CATHETER AND CANNULA ASSEMBLY

[75] Inventor: Henry G. Wallace, Colchester, United Kingdom

[73] Assignee: H. G. Wallace Ltd., Colchester, United Kingdom

[21] Appl. No.: 172,233

[22] Filed: Mar. 23, 1988

[30] Foreign Application Priority Data

Sep. 15, 1987 [GB] United Kingdom ............... 8721637

[51] Int. Cl.⁴ .......................................... A61M 25/00
[52] U.S. Cl. .................................... 604/48; 604/280; 128/774
[58] Field of Search ............... 604/117, 158, 165, 264, 604/280, 55, 54, 48; 128/658, 772

[56] References Cited

U.S. PATENT DOCUMENTS

| | | | |
|---|---|---|---|
| 1,995,051 | 3/1935 | Benson | 604/264 X |
| 3,094,124 | 6/1963 | Biftwell | 604/280 |
| 3,399,668 | 9/1968 | Lundgren | 604/280 X |
| 4,194,513 | 3/1980 | Rhines et al. | 604/55 X |
| 4,500,313 | 2/1985 | Young | 604/280 |
| 4,738,658 | 4/1988 | Magro et al. | 604/158 X |

Primary Examiner—Stephen C. Pellegrino
Attorney, Agent, or Firm—Laubscher, Presta & Laubscher

[57] ABSTRACT

The invention provides an assembly of a catheter and a cannula for cooperation therewith, wherein the catheter is provided with visible gradations disposed on the surface of the catheter adjacent its hub. The catheter cooperates with the cannula which is provided with gradations adjacent its distal tip. The arrangement in accordance with this invention allows for the accurate placement of small biological particles such as human embryos to appropriate body cavities.

4 Claims, 1 Drawing Sheet

CATHETER AND CANNULA ASSEMBLY

BACKGROUND OF THE INVENTION

The present invention relates to a catheter and cannula assembly particularly, although not exclusively, for use in medical practice.

Assemblies of a catheter sliding within a cannula are known for a number of applications. One of the difficulties which arises in the use thereof is that when the distal tip of the cannula has been urged into an opening, it is no longer possible to ascertain the precise depth of penetration of either the cannula or, in use, the catheter sliding within.

In vitro fertilization has been an established medical technique since 1978. An essential device used in placing embryos into the uterus of a recipient is a catheter which can be utilized to enter the cervical canal per vaginum and to deposit the embryos into the uterus without damage. Such a catheter needs to utilize a soft and flexible synthetic polymer in order to avoid trauma to the cervical canal; this of course presents problems in directing the catheter via the cervical canal.

This problem has, in part, been overcome by the utilization of a catheter having a generally rigid outer sheath which is provided so that during the initial direction of the catheter to the external os of the cervical canal, the sheath can be moved to protect the distal tip of the catheter. The catheter can therefore be carried by the cannula through the cervical canal as far as the internal cervical os whereupon the catheter can be moved into the uterine cavity. The catheter can then be advanced and the sheath retracted.

SUMMARY OF THE INVENTION

It has been found in use that the performance of this device can be improved if it can be readily ascertained, with the distal end of the cannula in situ, where the distal end of the catheter will be.

Accordingly the present invention provides an assembly of a catheter and a cannula therefor, characterized in that visible gradations are disposed on the surface of the catheter adjacent its hub.

In a preferred form of the invention, the cannula is substantially rigid and is provided with visible gradations adjacent its distal tip. Each of the cannula and catheter are preferably provided adjacent their first ends with hubs, said hubs being interlockable in a closed position such that the catheter is in its position of maximum extension. The catheter is most preferably soft and flexible and is provided with a terminal or side outlet constituted to limit trauma both externally to the uterine tissue, and internally to any embryos passing through the catheter. To this end it is preferred that the cannula is formed of a self-lubricating material such as "TEFLON®".

BRIEF DESCRIPTION OF THE DRAWING

The invention will now be illustrated, by way of illustration only, with reference to the accompanying drawing wherein.

DESCRIPTION OF THE PREFERRED EMBODIMENT

Figure 1:
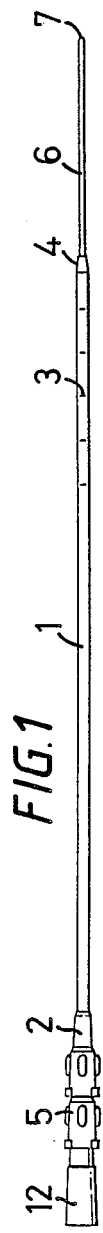
FIG. 1 is a side elevational view of the cannula/catheter assembly in its closed position.
Figure 2:
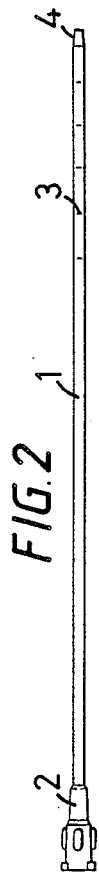
FIG. 2 is a side elevational view of the cannula.
Figure 3:
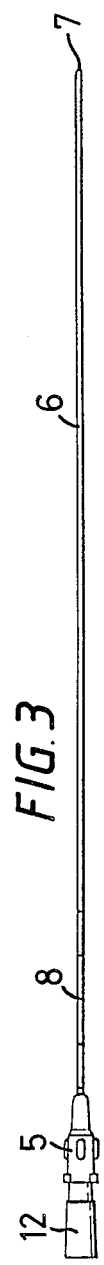
FIG. 3 is a side elevational view of the catheter.
Figure 4:
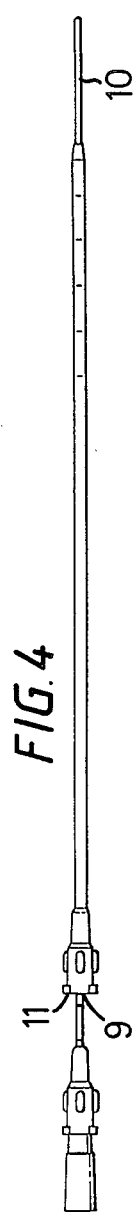
FIG. 4 is a side elevational view of the cannula and catheter assembly with the catheter withdrawn one graduation.

With reference to FIGS. 1 and 4 there is provided a cannula (1) being in the form of a hollow tube and provided towards its first end with a hub (2) provided with a series of axially extending fins to assist in manipulation. The distal end of the cannula (1) is provided at intervals of one centimeter with gradations (3) which are marked as a plurality of rings about the distal end, and which may be slightly indented into the outer surface thereof. The remote distal tip of the cannula (4) is chamfered for minimal trauma.

The cannula (1) is adapted to accommodate therewithin a catheter (6) having an external diameter such as to be an easy sliding fit within the cannula (1) and an internal diameter of a size to readily accommodate an embryo. The catheter (6) is provided at its one end with a hub (5) provided about its external surface with a plurality of axially extending fins to assist manipulation. The hub (5) is closed by a venting plug (12) which can be replaceably removed in order to gain access to the bore of the catheter (6). The catheter (6) is provided adjacent the hub (5) with a plurality of equally spaced gradations (8) which are clearly marked in a distinctive color, and which may be slightly indented into the surface of the material of the catheter. The hubs (2) and (5) are adapted such that they interlock in their closed position as shown in FIG. 1. This is done by arranging an interlocking annulus between the said hubs.

Figure 5:
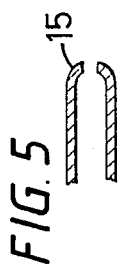
FIG. 5 is an enlarged vertical cross section through a catheter tip.

The distal end (7) of the catheter (6) is shown in FIG. 5. This is provided with a smoothly radiused chamfer (15) adapted to cause minimum trauma to the uterine tissues.

In use, the hubs (2) and (5) are disengaged and the cannula (1) is moved so that the distal ends of the catheter and cannula are co-incident. The cannula, which is formed of a generally rigid self-lubricating plastics material such as TEFLON® is advanced toward the external os of the cervical canal. With the distal end (4) of the cannula (1) positioned at the external os of the cervical canal, ideally the catheter (6) can be advanced so as to negotiate the cervical canal to the internal os into the uterus. However, often an obstruction or tortuous path is encountered in the cervical canal. In this instance the catheter (6) may be gently rotated within the cannula (1) to assist its advance.

However, since the catheter is soft, the advance of the distal tip (7) thereof can be readily obturated. In this instance the cannula (1) is gently advanced through the cervical canal to overcome obstruction or tortuous route so that the catheter (6) can pass into the uterus. It is however important that the cannula does not penetrate beyond the internal os and for this reason the gradation on its distal tip may be inspected to ensure that this does not occur. With the distal end of the catheter at the internal os of the uterus it is then possible to retract the cannula (1) while leaving the catheter in situ. This is a very delicate operation which is materially assisted by the gradation which are required so that it can be ensured that the retraction of the cannula is not associated with a commensurate retraction of the catheter. When the catheter is in situ and the cannula has been fully withdrawn the hubs (2) and (5) can be interlocked prior to the introduction of an embryo.

In this particular embodiment the catheter has a softness of approximately Durometer A scale 80 with a constant lumen of, for example 1.5 mm (0.06 inches). The terminal outlet (7) of the catheter (6) is shown in FIG. 5 as being axial. The outlet (7) may, however, be peripheral so long as it is sized and shaped to cause minimum trauma to embryos.

The catheter (6) in accordance with this embodiment of the invention is preferably formed of a flexible synthetic polymer, non-toxic to human embryos, sperm and oocytes as far as is possible.

The present invention provides, therefore, an assembly of a catheter and cannula, particularly for use in in vitro fertilization, but also for medical and other purposes.

The invention also provides a soft flexible catheter formed of a biologically acceptable synthetic polymer, said catheter being provided with a tube and a hub, the external face of the tube adjacent the hub being provided with a series of visible markings or indentations.

I claim:

1. An assembly of a catheter and a cannula therefor, said catheter and said cannula each having a first end and a second end, wherein visible gradations are disposed on the surface of the catheter adjacent a hub at its first end; characterized in that the cannula is substantially rigid and is provided with visible gradations adjacent its tip at the second end thereof.

2. An assembly according to claim 1, characterized in that each of the catheter and cannula are provided adjacent their first ends with hubs, said hubs being interlockable in a closed position so that the catheter is in its position of maximum extension.

3. An assembly according to claim 1, characterized in that the catheter is soft, flexible and is provided with a chamfered outlet at its second end.

4. An assembly according to claim 1, characterized in that the catheter is provided with a side outlet adjacent its second end.

* * * * *